United States Patent [19]

Williams

[11] 3,995,329
[45] Dec. 7, 1976

[54] FEMALE URINARY DEVICE
[76] Inventor: Clyde E. Williams, P.O. Box 527, Rancho Santa Fe, Calif. 92067
[22] Filed: Oct. 10, 1975
[21] Appl. No.: 621,360
[52] U.S. Cl. .................................. 4/110; 128/295
[51] Int. Cl.² ................ A47K 11/02; E03D 13/00
[58] Field of Search ............ 4/110, 112, 91, 1, 111; 128/2 F, 295, 350

[56] References Cited
UNITED STATES PATENTS

| | | | |
|---|---|---|---|
| 1,510,973 | 10/1924 | Bahan | 4/110 |
| 2,490,969 | 12/1949 | Kinyon | 4/110 |
| 2,690,568 | 10/1954 | Willis | 4/110 |
| 3,329,973 | 7/1967 | Bobbie | 16/105 |
| 3,351,050 | 11/1967 | Naftolin | 128/2 F |
| 3,512,185 | 5/1970 | Ellis | 4/110 |
| 3,556,102 | 1/1971 | Davis | 128/295 |
| 3,613,122 | 10/1971 | Gross et al. | 4/110 |
| 3,776,235 | 12/1973 | Ratcliffe et al. | 128/295 |
| 3,815,581 | 6/1974 | Lavin | 128/2 F |
| 3,864,759 | 2/1975 | Horiuchi | 4/110 |

*Primary Examiner*—Henry K. Artis
*Attorney, Agent, or Firm*—Duane C. Bowen

[57] ABSTRACT

A unitary body has an elongated lower portion with a fluid discharge passageway and an upper portion which has continuous sealing walls. Each side wall fits between a labia minora and a spread labia majora. The front wall is disposed slightly forward of the preputium clitoridis and the rear wall is disposed slightly forward of the pars intermedia. Side walls are concavely curved to generally match but somewhat distort abutted flesh. Flanges intermediate lower and upper portions form a resting surface for a pair of the user's phalanges in pressing the body into place.

11 Claims, 5 Drawing Figures

U.S. Patent    Dec. 7, 1976    3,995,329
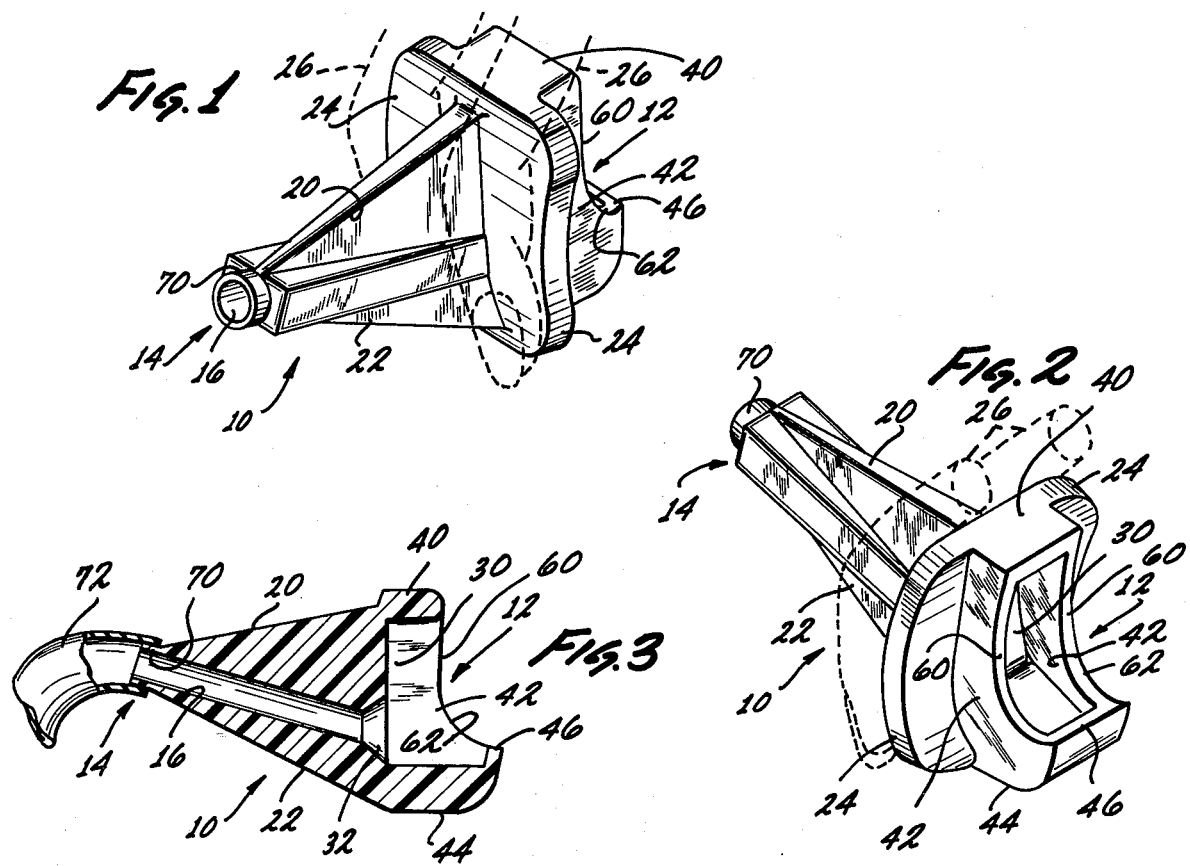
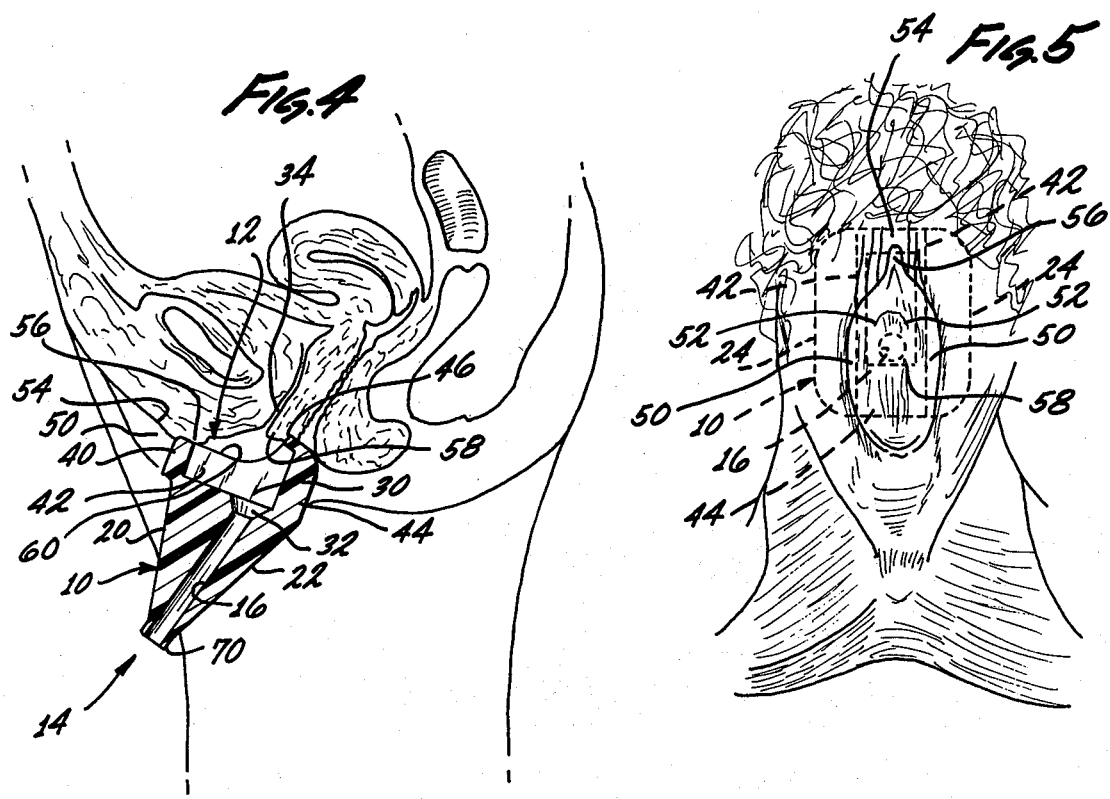

FEMALE URINARY DEVICE

BRIEF SUMMARY OF THE INVENTION, BACKGROUND AND OBJECTIVES

My invention relates to a urinary device permitting the female to urinate while standing and which seals against the body and directs urine out a fluid discharge passageway.

Prior patents such as U.S. Pat. Nos. 2,690,568, 3,613,122, 3,864,759, 3,815,581, 3,556,102 and 3,329,973 have dealt more or less with the same problem addressed in this invention. Briefly, a principal problem concerns urinating in public facilities when the toilet seats are unsanitary. This problem would be solved if the female could urinate standing, like a male, and direct the urine away from the body, into a toilet or urinal, without substantial soiling of the body or the clothing with urine. There are other conditions when this would be advantageous, i.e., when a urine sample is to be obtained with minimum adulteration, or when there is a health problem caused in an individual because the bladder is less completely voided in the sitting position than in the standing position. A somewhat similar problem is involved with a bedridden patient.

A chief problem in providing a device so that the female can urinate standing, that does not appear to have been solved in the prior art, is to adequately seal against urine excape other than through the fluid discharge passageway of the device. If there is soiling of the clothing or of the body outside of the device, then the structure is impractical for most purposes. To repeat, the mandatory requirement is an effective seal and nothing less will do, and to provide a structure achieving an effective seal is an object of my invention.

Other objectives of my invention include: to provide such a device which best adapts to the body in achieving a seal, to devise a structure achieving both sanitation and effectiveness, to devise a structure easily and simply usable but providing maximum effectiveness, and to provide an economical and durable construction.

My invention will be best understood, together with additional objectives and advantages thereof, from the following description, read with reference to the drawings, in which:

FIG. 1 is a perspective view of a specific embodiment of my new urinary device. Manual holding of the device is illustrated by a pair of the user's phalanges shown in dashed lines.

FIG. 2 is like FIG. 1 but viewed at a different angle.

FIG. 3 is a sectional side view. The figure also shows portions of a tube that would used with the device for a bedridden patient.

FIG. 4 shows the device in use, the device being viewed in section and the female body being shown in fragmentary form.

FIG. 5 is a view of urinary and adjacent areas of the female body. The orientation of the urinary device is depicted in dashed lines.

The urinary device 10 is preferably formed of a material having some but limited resilience. By this I mean the material gives enough to form a seal but preferably otherwise the material is substantially undistorted in use; and, instead, the pressure of the device makes the abutted flesh yield to conform to the device rather than the reverse. It should be obvious that a urinary device of this type has limited if any usefulness if it does not form an adequate seal. A general description of a suitable material would be one having the resilience of fairly hard rubber. Device 10 can be made of a number of materials, particularly a suitable plastic or a natural or artificial rubber.

A specific example of a suitable material is a product of Dow Corning Corporation, Midland, Mich., a SILASTIC RTV mold-making silicone rubber, particulary SILASTIC A with Dow Corning RTV catalyst 4 (a 100 percent active catalyst), pre-tested stannous octoate. After vulcanizing for 72 hours at 77F, the ASTM D 176 durometer hardness, Shore A, is 45, the ASTM D 412 tensile strength, psi, is 400, the ASTM D 412 elongation, percent, is 180, and the ASTM D 624 tear strength, die B, ppi, is 15.

A silicone rubber is a particularly good selection because of good water repellency. Devise 10 can be rinsed off after use. To the extent the material is not wetted, due to its water repellency, the problem of soiling is reduced and cleaning by rinsing is made easier. It is a feature of my invention to use a water repellent material, such as silicon rubber. Sterilization may be a particular concern in a hospital or the like, particularly in use with bedridden patients, and the silicone rubber specified can be sterilized in alcohol or by steam in an autoclave.

Note that sealing capability has a relationship to material hardness. The 45 Durometer hardness value cited above with SILASTIC A is suitable. The sealing function in the present application concerns generally the same factors as sealing between parts in general against liquid leakage. Here the seal is not against substantially pressurized liquids. In general a seal between parts requires more pressure to the extent the parts do not conform and to the extent the sealing material does not give. In the present application the body tissues will readily give to conform but undue pressure is objectionable. So that it is preferred to use a material with a Durometer reading comparable to that cited so that the sealing will be accomplished with less pressure than would be needed with a harder materials. The yielding of the flesh helps make the seal but the abutted edges of device 10 press against irregular flesh areas, folds of flesh, etc., so that it is best not to rely on flesh conformation in order to make a seal, particularly in view of the desirability of avoiding a requirement of undue pressure. A balance must be made between a material having a Durometer hardness suitable to make a seal and a material not having sufficient rigidity to generally keep its shape in order more to force flesh to conform to its form rather than the reverse. The strength of material values given above for SILASTIC A are suitable.

The body of device 10 has a urine collecting and sealing upper portion 12 and a urine discharging lower portion 14. The expressions "upper" and "lower" are used for convenience of description, but it will be noted from FIG. 4 that lower portion 14 is more completely described during use as being elongated in a direction extending downwardly and somewhat forwardly from upper portion 12, so that its fluid passageway 16 is directed to discharge downwardly and somewhat forwardly. Passageway 16 should be a minimum of ¼ inch in diameter and preferably is 5/16 inch in diameter, as it is desirable to fully accommodate urine discharge from the body without any backup resulting from a limitation in the carrying capacity of passageway 16.

A pair of triangular reinforcing ribs 20, 22 join the lower tubular shape to the upper portion 12. Upper portion 12 has a pair of flanges 24 (slightly curved in side view) extending to each side forming resting surfaces for a pair of phalanges 26 of the user in pressing body 10 into place, i.e., the first and second or second and third fingers may be most convenient.

Upper portion 12 has a central fluid receiving space 30, preferably joining pasageway 16 via a transition portion 32. Exact alignment of the female external urethral orifice 34 with passageway 16 is improbable in first use, although the possibility is not discarded that enough use of the device will result in learning to generally align passageway 16 with discharge from orifice 34 because of the sensory feedback of splash back. In any case, space 30 is adapted to receive urine before passing out passageway 16 and is large enough (about ⅝ inch × 1 11/32 inch, in face view, is suitable) to accommodate substantial misalignment.

Space 30 is bounded at its forward end by a wall 40, at each side by walls 42, and at its rear end by wall 46. The edges of these walls form a continuous sealing surface with adjacent portions fairing into one another. These walls are directed mostly parallel to passageway 16 (walls 42 being parallel and wall 40 deviating at a sharply acute angle) but the rear portion has a lower wall section 44 deviating from the axis of passageway 16 at a sharply acute angle and joining with rear wall 46 which is directed generally transverse relative to the axis of passageway 16. Passageway 16 is a convenient reference but could extend at a different angle relative to upper portion 12 but the relative relationships among walls 40–46 described preferably should be maintained.

Device 10 is designed for general, usual alignment of each wall 42 between one of the labia majora 50 (somewhat spread by the user) and the adjacent labia minora 52, with the edge of front wall 40 bearing on the mons pubis 54 immediately forward of the preputium clitoridis 56, and with the edge of wall 46 bearing immediately forward of the pars intermedia 58.

It is important that upper portion 12 be properly sized. Walls 42 must be located each to fit between a labia minora and a manually spread labia majora. Central dimensions will be given, in case the walls do not make a geometrical rectangle. The central dimension between the outer surfaces of walls 42 is preferably about 0.90 inch, with a maximum dimension of 1.00 inch and with a minimum dimension of 0.70 inch. If the dimension is 0.90 inch and the wall thicknesses are 0.125 inch, the width of space 30 will be 0.65 inch. The central dimension between the inner surfaces (innner corners, as the walls are relatively tipped) of walls 40, 46 is preferably about 1 11/32 inch, with a minimum of 1.00 inch. Factors to be considered include capacity of space 30, but the above dimensions more concern proper fit and effective operation even if the device is somewhat mislocated relative to urethal orifice 34. In considering the distance between walls 40, 46 the minimum internal dimension is the most important. If the distance is longer than that considered ideal, the main effect may be location of front wall 40 further forward of the preputium clitoridis than otherwise would be the case, which would not be a critical matter, although it is important not to locate rear wall 46 too far rearwardly, over the vaginal orifice.

The edges of side walls 42 are concavely curved, seen particularly in FIG. 3, with a forward major portion 60 relatively gradually curving and extending primarily laterally relative to the axis of passageway 16, and with a rear minor portion 62 relatively abruptly curving and extending primarily longitudinally relative to the axis of passageway 16. The reason for the described concave curving of the edges of side walls 42 is to generally match the curve of abutted flesh, primarily mucous membrane, particularly of the labia majora and labia minora, but being, preferably, somewhat more abruptly curved so as to produce some flesh distortion, compression or displacement in pressing body 10 into place, in order to help perfect particularly side seals by the edges of walls 42. It is difficult to depict or describe affected areas of flesh, due to the complexity of body structure, i.e., the posterior ends of the labia majora appear to become lost in the neighboring integument, but the configuration of walls 42 described achieve a sufficient seal when pressed into place with moderate pressure. The preferred radius of portion 62 is about 0.678 inch, with a maximum radius of 1.00 inch and with a minimum radius of 0.50 inch. The radiuses are experimentally derived, rather than being based on body measurements, because, as mentioned, of the complexity of body structure involved. In fact, the curvature 62 may partly accommodate variations in the affected female anatomy.

The operation of my urinary device 10 has been described in connection with the foregoing structural description. The user can carry device 10 in a purse for use usually with unsanitary public facilities. If the woman has a health problem due to incomplete blader voiding, of course the device also may be used in the home. It is best used in a standing position with the legs somewhat spread (not closed). Some manual spreading of the labia majora will facilate location of walls 42 between labia majora and labia minora. The locations of walls 40 and lip 46 have already been described. Exact location is not required but after a period of use effective locations will become automatic. Moderate manual presure will effect a sufficient seal. After use the device 10 may be rinsed off, but cleaning after each use will be a minor problem due to water repellency.

Another use of device 10 is with a bedridden patient. For that purpose, lower portion 14 terminates at its lower end with a section 70 of annular cross-section so that a tube 72 can be snapped onto annular section 70 for discharge of urine from tube 72 into a suitable receptacle.

Having thus described my invention, I do not wish to be understood as limiting myself to exact details of the structure described. Instead, I wish to cover those modifications of my invention which will occur to those skilled in the art upon learning of my invention, and which properly are within the scope of my invention.

I claim:
1. A urinary device for females, comprising:
   a. a urinary body having a urine collecting and sealing upper portion and having a urine discharging lower portion,
   b. said lower portion extending downwardly from said upper portion and being elongated in a downward direction, said lower portion having a fluid passageway therethrough for urine discharge,
   c. said upper portion terminating in front, rear and side walls projecting upwardly from the end of said upper portion opposite to said lower portion and forming a continuous wall boundary of said upper portion of generally rectangular configuration, said front and side walls being generally parallel to the axis of said fluid passageway and said rear wall extending at an abrupt angle to said axis and extending in a direction partly forwardly, the upper edges of each side wall concavely curving on a line having a forward and major portion extending primarily laterally of said axis and relatively gradually curving and a rear minor portion extending primarily longitudinally of said axis and relatively abruptly curving, said side walls having such spacing as to each fit between one spread labia majora and the adjacent labia minora of an average adult female and said front and rear walls having such spacing as to extend generally from the mons pubis immediately forward of the preputium clitoridis to immediately forward of the pars intermedia, said concavely curving of said side wall edges generally matching the curve of the flesh of the average adult female in the abutted areas but being more abruptly curved than said flesh so as to produce some flesh distortion in pressing said body into place to help perfect a seal by said walls, and d. said fluid passageway communicating with the space between said walls.

2. The subject matter of claim 1 in which there is a flange to each side of said upper portion of said body spaced from said edges of said walls forming a resting surface for a pair of phalanges of the user in pressing said body into place.

3. The subject matter of claim 1 in which at least said edges of said walls are of rubber-like resiliency to assist in forming a seal with abutted flesh.

4. The subject matter of claim 1 in which said body is formed of material of high water repellency.

5. The subject matter of claim 1 in which there are a pair of triangular reinforcing ribs to the rear and forward sides of said lower portion and joining with said upper portion to strengthen the structure.

6. The subject matter of claim 1 in which said lower portion terminates at its lower end with a section of annular cross-section and a tube fit onto said section of annular cross-section for discharge of urine from the tube to a receptacle for a bedridden person.

7. The subject matter of claim 1 in which there is a lower wall section extending generally parallel to said axis from which said rear wall extends whereby extra urine capacity is provided in said space between said walls.

8. A urinary device for females, comprising:
a. a body having a urine collecting and sealing upper portion and having a urine discharging lower portion,
b. said urine discharging lower portion having a fluid passageway therethrough for urine discharge,
c. said urine collecting and sealing upper portion including walls projecting upwardly from the end of said upper portion opposite to said lower portion forming a continuous wall boundry having a continuous wall edge with adjacent portions fairing into one another and including side wall portions spaced apart such distance that each will fit between a spread labia majora and the adjacent labia minora and including front and rear wall portions having such spacing as to extend generally from the mons pubis immediately forward of the preputium clitoridis to immediately forward of the pars intermedia, said wall edge of each side wall portion concavely curving on a line having a forward and major portion relatively gradually curving and a rear and minor portion relatively abruptly curving, said concavely curving of said wall edges of said side wall portions generally matching the curve of the flesh of the average adult female in the abutted areas but being more abruptly curved than said flesh so as to produce some flesh distortion in pressing said body into place to help perfect a seal by said walls, and
d. said fluid passageway communicating with the space between said side walls.

9. The subject matter of claim 8 in which the relatively abrupt curve of said rear and minor portion of the wall edge of each side wall portion has a maximum radius of 1.00 inch and a minimum radius of 0.50 inch.

10. A urinary device for females, comprising:
a. a body having a urine collecting and sealing upper portion and having a urine discharging lower portion,
b. said urine discharging lower portion having a fluid passageway therethrough for urine discharge,
c. said urine collecting and sealing upper portion including walls projecting upwardly from the end of said upper portion opposite to said lower portion forming a continuous wall boundry having a continuous wall edge with adjacent portions fairing into one another and including side wall portions spaced apart such distance that each will fit between a spread labia majora and the adjacent labia minora and including front and rear wall portions having such spacing as to extend generally from the mons pubis immediately forward of the preputium clitoridis to immediately forward of the pars intermedia, and
d. said fluid passageway communicating with the space between said walls.

11. The subject matter of claim 10 in which the central distance across said upper portion between the outer surfaces of said side wall portions is a maximum of 1.00 inch and a minimum of 0.70 inch and the central distance across said upper portion between the edges of said front and rear wall portions is a minimum of 1.00 inch.

* * * * *